United States Patent [19]
Jacobson et al.

[11] Patent Number: 5,281,816
[45] Date of Patent: Jan. 25, 1994

[54] METHOD AND APPARATUS FOR DETECTING HYDROCARBON VAPORS IN A MONITORED AREA

[75] Inventors: Esther Jacobson; Yechiel Spector; Ephraim Goldberg, all of Tel Aviv, Israel

[73] Assignee: Spectronix Ltd., Tel Aviv, Israel

[21] Appl. No.: 863,663

[22] Filed: Apr. 6, 1992

[30] Foreign Application Priority Data

Jul. 4, 1991 [IL] Israel ..................... 98729

[51] Int. Cl.$^5$ ......................................... G01N 21/25
[52] U.S. Cl. ................... 250/339; 250/338.5; 250/343; 250/373; 340/600; 340/632
[58] Field of Search ............ 250/373, 338.5, 339, 250/372, 345, 343; 340/600, 632

[56] References Cited

U.S. PATENT DOCUMENTS

| | | | |
|---|---|---|---|
| 3,743,426 | 7/1973 | Steinberg | 250/345 |
| 4,220,415 | 9/1980 | Staab et al. | 250/343 |
| 4,370,553 | 1/1983 | Waycaster et al. | 250/343 |
| 4,437,004 | 3/1984 | Passaro et al. | 250/343 |
| 4,496,431 | 2/1991 | Bonne et al. | 250/339 |
| 4,496,840 | 1/1985 | Fabinski et al. | 250/345 |
| 4,958,076 | 9/1990 | Bonne et al. | 250/339 |
| 5,210,702 | 5/1993 | Bishop et al. | 250/338.5 |

FOREIGN PATENT DOCUMENTS

| | | | |
|---|---|---|---|
| 230692 | 8/1987 | European Pat. Off. | 250/373 |
| 45-11599 | 4/1970 | Japan | 250/373 |
| 2178841 | 2/1987 | United Kingdom | 250/373 |

OTHER PUBLICATIONS

Greinke, R. A., et al., "Development of a Gas Chromatographic-UV Absorption Spectrometric Method for Monitoring Petroleum Pitch Volatiles in the Environment", Anal. Chem. vol. 47 #13 Nov. 1975 pp. 2151-2155.

Primary Examiner—Constantine Hannaher
Assistant Examiner—Drew A. Dunn
Attorney, Agent, or Firm—Benjamin J. Barish

[57] ABSTRACT

A method and apparatus for detecting the presence of a predetermined hydrocarbon vapour of a predetermined concentration in a monitored area by: exposing gas in or from the monitored area to radiation from a Xenon flashlamp which includes ultraviolet radiation of a predetermined ultraviolet spectral range and infrared radiation of a predetermined infrared spectral range; detecting the radiation after having passed through the gas; and comparing the detected radiation with a reference of predetermined attenuation characteristics of the hydrocarbon vapour and concentration in the respective ultraviolet and infrared spectral range.

32 Claims, 5 Drawing Sheets

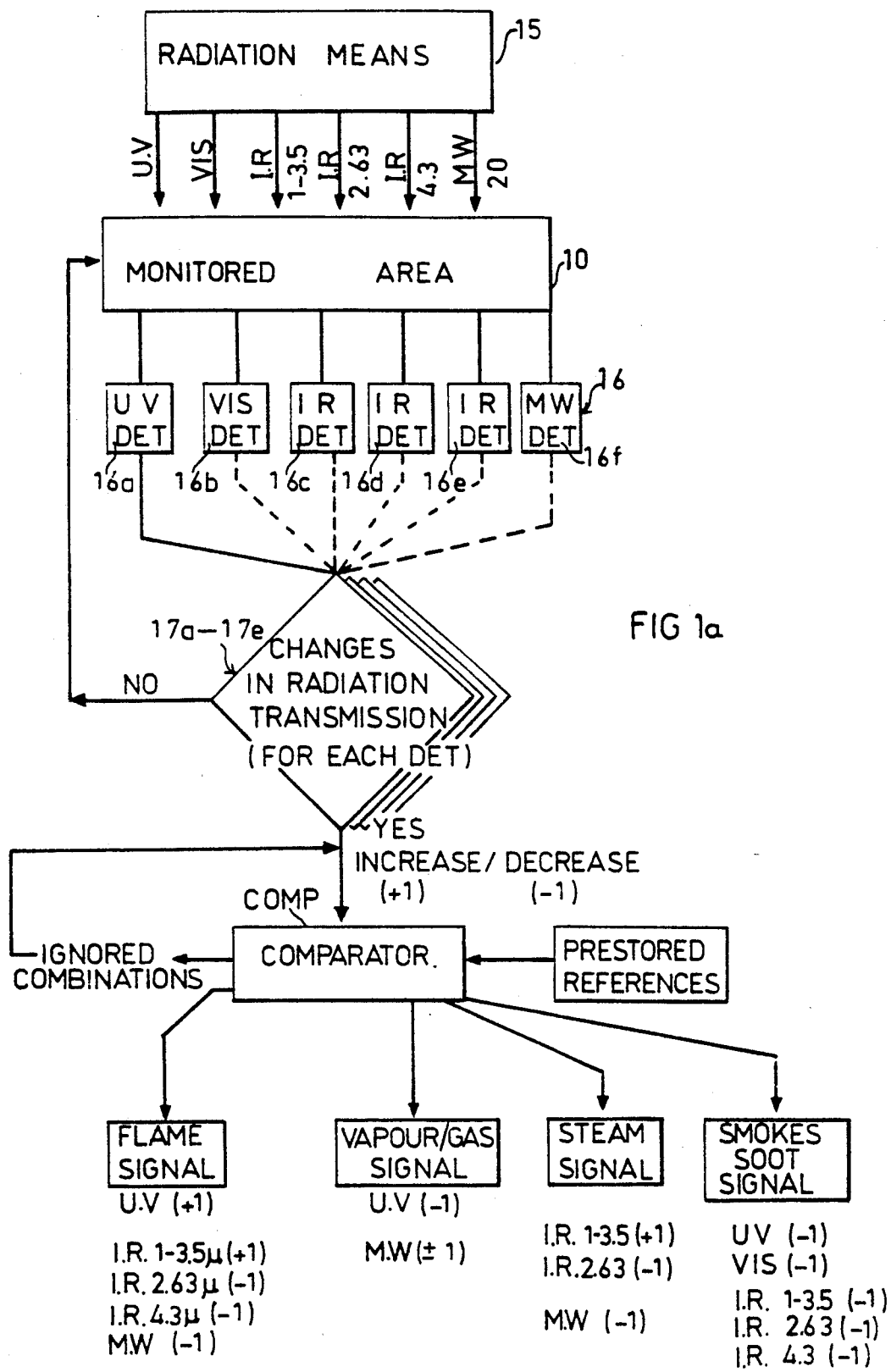

METHOD AND APPARATUS FOR DETECTING HYDROCARBON VAPORS IN A MONITORED AREA

FIELD AND BACKGROUND OF THE INVENTION

The present invention relates to a method, and also to apparatus, for detecting the presence of predetermined hydrocarbon vapours in a monitored area. The invention is particularly useful for detecting flammable hydrocarbon vapours when they are present at a concentration which might indicate a possible flammable or explosive atmosphere, and the invention is therefore described with respect to this application.

At the present time, analysis of an atmosphere to determine the concentration of a flammable-vapour therein is commonly carried out by combustion methods. The flammable vapour is fed (with air) into a combustion chamber where it is exposed to a controlled flame. When the vapour hits the flame, it burns and gives off heat which is sensed by a resistance temperature detector (RTD), or by a flame ionization detector (FID), which enables the concentration of flammable vapours to be determined.

Another technique, based on total organic-carbon (TOC) analysis, combines combustion with infrared absorption to determine the organic carbon content. The sample stream is oxidized to produce $CO_2$, and the amount of $CO_2$ is measured according to $CO_2$ infrared analysis techniques.

However, the above known techniques of flammable-vapour analysis require exact calibration of the specific material to be detected, are very sensitive to other compounds with similar behaviour, require long time measurements (response time usually greater than one minute), are expensive and cumbersome, and/or lack versatility in implementation.

It has also been proposed to detect a fire optically by the use of a visible wavelength band detector alone, or in combination with an infrared wavelength band detector (see for example U.S. Pat. No. 4,156,816 of May 29, 1979), and also to use a visible wavelength band detector for detecting various types of fluorocarbon gasses which may escape the environment (see for example U.S. Pat. No. 4,891,518 of Jan. 2, 1990). Other known types of vapour or gas analyzers based on the detection of radiation, or the attenuation of radiation by the gas or vapour being analyzed, are described in U.S. Pat. Nos. 4,385,516 of May 31, 1983, 4,517,161 of May 14, 1985 and 4,964,309 of Oct. 23, 1990. A further technique of analyzing a gas or vapour, based on measuring the strenght of acoustic resonance in a chamber containing a sample of the gas, is described in U.S. Pat. No. 4,055,764 of Oct. 25, 1977.

OBJECTS AND BRIEF SUMMARY OF THE INVENTION

An object of the present invention is to provide a novel method and apparatus having advantages in some or all of the above respects and particularly useful for detecting the presence of a predetermined hydrocarbon vapour in a monitored area.

According to the present invention, there is provided a method of detecting the presence of a predetermined hydrocarbon vapour of a predetermined concentration in a monitored area, comprising: exposing gas in or from the monitored area to radiation emitted from a flashlamp which emits both ultraviolet radiation and infrared radiation; detecting ultraviolet radiation within a predetermined ultraviolet spectral range, and infrared radiation within a predetermined infrared spectral range after the radiation emitted from the flashlamp has passed through the gas; and comparing the detected ultraviolet radiation and infrared radiation with a reference of predetermined attenuation characteristics of the hydrocarbon vapour and concentration in the ultraviolet and infrared spectral ranges.

According to preferred embodiments of the invention described below, the ultraviolet spectral band is from 0.1–0.4 $\mu$m. Detected radiation below the reference provides an indication of the presence of the predetermined hydrocarbon vapour in the monitored atmosphere at a concentration producing a possible flammable or explosive atmosphere.

The method is particularly useful for detecting flammable hydrocarbon vapours in a hazardous area, e.g., in the storage area of petrol chemicals, engine rooms where leaks of fuel create an explosion or fire hazard, etc. Such detection is very important to provide a signal or alarm of a hazardous condition, or to automatically actuate a fire extinguishing system or other control in order to remove the hazardous condition.

For example, it is well known that the alkanes (straight paraffines) absorb radiation in the far-ultraviolet and mid-infrared spectral ranges (specifically 0.16–0.14 $\mu$m and 3.5 $\mu$m), whereas double-bonded alkenes and aromatics (e.g., benzene, naphtalene) absorb radiation more readily in the near-ultraviolet (0.2–0.3 $\mu$m), and in the mid-infrared (3.5 $\mu$m, 6–7 $\mu$m) range. Since most flammable fuels (e.g., gasolene, kerosene, diesel fuel) contain the above-mentioned three chemical groups, the logic circuitry could be supplied with their spectral signatures, defined by their attenuation of the radiation in their respective spectral bands, in order to permit a determination to be made whether they are present in the specified concentration in the monitored area, and to provide the appropriate signal, alarm or control as a result of such determination.

According to further features in the preferred embodiments of the invention described below, the infrared spectral range is selected to be 1–3.5 $\mu$m. Within this broad range, a flame, smoke or water vapour within the monitored area will increase the detected radiation, as compared to the reference, and therefore detecting the infrared radiation within this spectral range can also be used to indicate the presence of a flame, smoke or water vapour in the monitored area. The predetermined infrared spectral range may include the 2.63 $\mu$m band and the 4.3 $\mu$m band. Detecting radiation below the reference in the 2.63 $\mu$m band provides an indication of the presence of water vapour, flame and/or smoke in the monitored area; and detecting radiation above the reference in the 4.3 $\mu$m band provides an indication of the presence of flame and/or smoke in the monitored area.

According to further features in the described embodiments, the radiation to which the gas is exposed also includes visible light from the 0.4–0.8 $\mu$m spectral range, and the detected radiation is also compared with a reference of predetermined attenuation characteristics in the visible light band. Detecting radiation above the reference indicates the presence of water vapour or a flame in the monitored area, and detecting radiation below the reference indicates smoke and/or soot particles in the monitored area.

According to a still further feature in the described preferred embodiments, the radiation to which the gas is exposed also includes radiation in the microwave spectral range, and the detected radiation is also compared with a reference of predetermined attenuation characteristics in the microwave spectral range. Detecting radiation below the reference indicates the presence of water vapour and/or a flame in the monitored area.

The invention also provides apparatus for detecting the presence of a predetermined hydrocarobon vapour of a predetermined concentration in a monitored area, comprising: flashlamp radiation means which emits both ultraviolet radiation and infrared radiation; means for exposing gas in or from the monitored area to the radiation emitted by the flashlamp radiation means; detector means for detecting ultraviolet radiation within a predetermined ultraviolet spectral range, and infrared radiation within a predetermined infrared spectral range, after the radiation emitted from the flashlamp has passed through the gas; and comparing means for comparing the detected ultraviolet and radiation infrared radiation with a reference of predetermined attenuation characteristics of the hydrocarbon vapour and concentration in the ultraviolet and infrared spectral ranges.

Further features and advantages of the invention will be apparent from the description below.

BRIEF DESCRIPTION OF THE DRAWINGS

The invention is herein described, by way of example only, with reference to the accompanying drawings, wherein:

FIG. 1a is a flow chart illustrating the operation of the logical circuitry in the system of FIG. 1, as well as in the systems of FIGS. 2-5.

DESCRIPTION OF PREFERRED EMBODIMENTS

Figure 1:
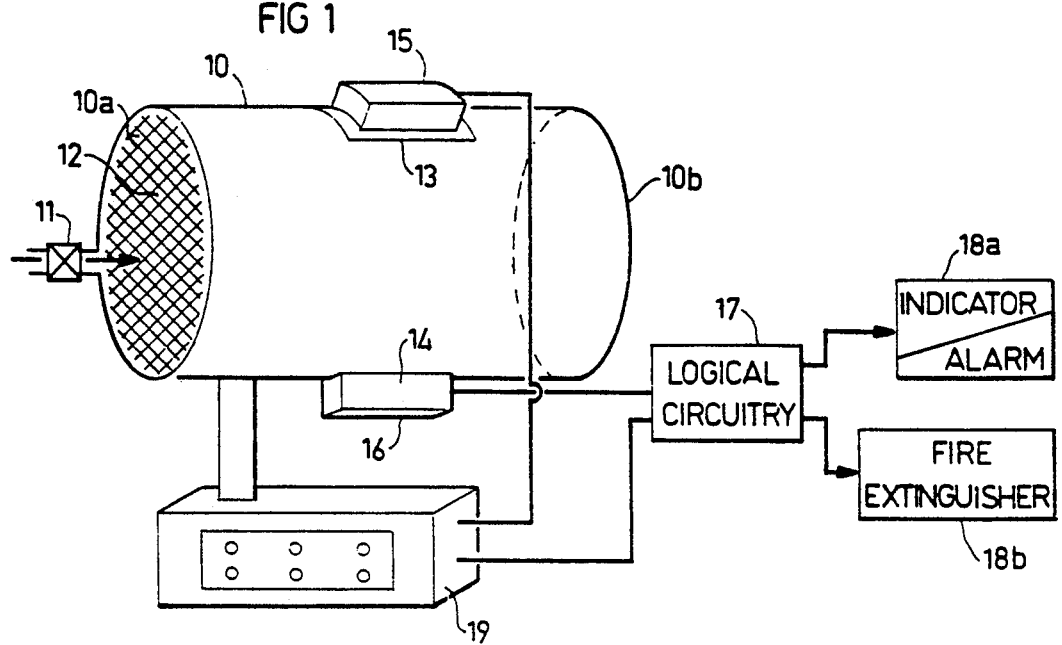
FIGS. 1-5 illustrate five detector systems constructed in accordance with the present invention.

The System of FIGS. 1 and 1a

The detector system illustrated in FIG. 1 includes a test chamber 10 having an inlet 10a connected to receive air, or other gas, from the monitored area by means of a pump 11 and/or a semipermeable membrane 12. The air flows through a flowpath in test chamber 10 to its outlet 10b. As will be described more particularly below, the test chamber 10 includes apparatus for detecting the presence of one or more predetermined hydrocarbon vapours in a predetermined concentration to provide an indication of whether there may be a possible flammable or explosive atmosphere in the monitored area.

The test chamber 10 is formed on its opposite sides with two windows 13, 14 located in alignment with each other along an axis extending transversely to the flowpath of the air through the test chamber. An ultraviolet radiation unit 15 is located in alignment with window 13, and a detector unit 16 is located in alignment with window 14. The output of detector unit 16 is fed to a control logic circuitry 17, which outputs control signals to an indicator or alarm unit 18a, and/or to a fire extinguisher unit 18b.

The overall electrical system is powered and controlled by a processor 19 connected to the radiation unit 15 and also to the control logic circuitry 17. Thus, processor 19 energizes the radiation unit 15 with a modulating (or chopping) signal of a predetermined frequency. The modulating signal is also fed to the control logic circuitry 17 so as to gate the input of the logic circuitry 17 from the radiation detector 14 at the same frequency, and thereby to filter out spurious signals from the radiation detector.

The radiation unit 15 is selected to expose the gas flowing through the test chamber 10 to ultraviolet radiation of a predetermined ultraviolet spectral range. The radiation unit 15 may be a deuterium lamp, a mercury lamp, a laser diode, or any other source capable of radiating at the required ultraviolet spectral range. The detector unit 16 thus detects the radiation from the radiation unit 15 after it has passed through the gas within the test chamber 10 and provides an electrical output corresponding to the radiation after it has been attenuated by the gas within the test chamber.

Processor 19 also feeds to the logic circuitry 17 prestored reference data corresponding to the attentuation characteristics of predetermined flammable hydrocarbon vapours in the spectral range being examined and in a specified predetermined concentration, e.g., one which might create a hazardous condition in the monitored area. The logic circuitry 17 then compares the data received from the radiation detector unit 16 with the reference data fed from the processor 19 and provides an electrical output indicative of the presence and concentration of each one of the predetermined flammable organic vapours in the gas passing through the test chamber 10.

Whenever logic circuitry 17 has thus determined that one of the predetermined flammable vapours is present in the test chamber 10 in a concentration indicating a hazardous condition in the monitored area supplying the gas to the test chamber, it outputs an electrical signal to indicator/alarm unit 18a to indicate this hazardous condition, and/or outputs an electrical signal to the fire extinguisher 18b to automatically actuate it and thereby to prevent a fire or explosion from occurring, or to suppress one if it has occurred.

It will thus be seen that so long as the gas within the test chamber 10 does not include one of the predetermined hydrocarbon vapours in a hazardous concentration, the logic circuitry 17 will output a "no-alarm" signal to units 18a, 18b. However, if test chamber 10 is found to contain one of the predetermined hydrocarbon vapours in a hazardous concentration, the logic circuit will output an "alarm" signal to the indicator/alarm unit unit 18a, and/or to the fire extinguisher 18b.

Mathematically, the attenuation is calculated according to Beer-Lambert law:

$$\frac{I_t}{I_o} = e^{-k \cdot p \cdot l}$$

where:
$I_t$ is the transmitted radiation recorded at the detector at each time interval t;
$I_o$ is the original radiation transmitted by the radiation source (and recorded at the detector when no absorbing vapour is present);
k is absorption coefficient of the vapour;
p is the vapour pressure (or concentration); and
l is the optical path (the distance from the radiation source to the detector).

The radiation unit 15 is rich in radiation in the ultraviolet spectral range of 0.1-0.4 μm, and particularly in the narrow band of 0.15-0.3 μm. However, this radiation unit may include radiation of other spectral ranges in order to better discriminate between the predetermined hydrocarbon vapours and/or other matter which may be in the monitored area, such as water vapour, flame, smoke and/or soot particles. Radiation in the visible spectral range of 0.4-0.8 μm, in the broad infrared spectral range of 1-3.5 μm and particularly in the narrow bands of 2.63 μm and 4.3 μm, respectively, and in the microwave range of 20 cm (1.4 GHz), have been found particularly effective to discriminate between hydrocarbon (fuel) vapours, water vapour, flames, smoke and soot particles. Following is a table showing how each of these in the monitored area influences the detected radiation changes:

the detector 16a-16e are fed to the logic circuit 17 which includes a circuit 17a-17e to measure the change in radiation transmission through the monitored area, and if there is a significant increase or decrease, such increase or decrease is fed to a comparator COMP which compares the radiation from the prestored references (prestored in processor 19) representing the attenuation characteristics in the respective spectral range for the particular condition to be detected, and outputs binary values corresponding to the results of these comparisons.

Thus, as shown in the flow chart of FIG. 1a, (a) a flame condition is indicated when the ultraviolet detector 16a, the visible detector 16b, and the infrared detector 16c for the broad spectral range of 1-3.5 μm, all detect radiation above the reference, and the other three detectors 16c, 16d, 16e detect radiation below the

| | INFLUENCE OF ATMOSPHERE'S COMPOSITION ON RADIATION CHANGES | | | | | |
|---|---|---|---|---|---|---|
| | U.V. Spectral Range | | I.R. Spectral Range (0.8-20 μm) | | | |
| ATMOSPHERE'S COMPOSITION | (0.1-0.4 μm) Specific Narrow Band 0.15-0.3 μm | Visible (0.4-0.8 μm) | I.R. Specific Large Band (1-3.5 μm) | I.R. Narrow Bands | | M W 1.4 GHz ($\lambda$ = 20 cm) |
| | | | | 2.63 μm | 4.3 μm | |
| FUEL VAPOUR/ GAS | ↓ strong absorption (−1) | - no change (0) | ∼small change (0) | - no change (0) | - no change (0) | ↑ different dielectric constant causes changes in radiation transmission (similar to "lens like" effect) (±1) |
| WATER ($H_2O$) & STEAM RELEASE | - no change (0) | - no change (slightly lower visibility) (0) | ↑ increase due to heated steam release (+1) | ↓ strong absorption (−1) | ↓ small absorption (0) | ↓ absorption (−1) |
| FLAMES | ↑ increase in radiation (due to flame U.V. radiation) (+1) | ↑ increase in radiation (+1) | ↑ increase due to heat radiation from flame (+1) | ↓ absorption due to $H_2O$ flame product (−1) | ↓ absorption due to $CO_2$ flame product (−1) | ↓ absorption due to electrons/ions in flame (−1) |
| SMOKE COLD | ↓ blockage of radiation according to smoke particles size and concentration (−1) | ↓ blockage of radiation according to smoke particles size and concentration (−1) | ∼small change (0) | ↓ absorption (−1) | ↓ absorption (−1) | ∼small change (0) |
| SMOKE HOT | ↓ blockage of radiation according to smoke particles size and concentration (−1) | ↓ blockage of radiation according to smoke particles size and concentration (−1) | ↑ increase due to head radiation (+1) | ↓ strong absorption (−1) | ↓ absorption (−1) | ∼small change (0) |
| SOOT (PARTICLES) | ↓ blockage of radiation according to smoke particles size and concentration (−1) | ↓ blockage of radiation according to smoke particles size and concentration (−1) | ∼small change (depends on particle size, and temp.) (0) | ∼small change (0) | ∼small change (0) | ∼small change (depends on particle size and concentration) (0) |

If the apparatus is to detect, and discriminate between, some or all of the foregoing influences in the monitored area, the processor 19 would store reference data corresponding to the attenuation characteristics of the particular condition to be detected in the respective spectral range at which that condition is to be detected. The ouput of the logic circuit 17 would thus provide an indication of the presence or absence of any of these conditions according to the above table.

FIG. 1a is a flow diagram illustrating how each of these conditions may be detected by the logic circuit 17 when the radiation unit radiates all the spectral ranges as set forth in the above table. Thus, as shown in the flow chart of FIG. 1a, the radiation means 15 emits radiation in each of the six spectral ranges included in the above table through the monitored area, and the detector unit 16 includes a detector 16a-16e which is sensitive to each of these spectral ranges. The outputs of reference; (b) a hydrocarbon or gas vapour condition is indicated when the ultraviolet detector 16a detects radiation in the ultraviolet range below the reference, and the microwave detector 16e detects microwave radiation in the respective spectral range either above or below the reference; (c) a water vapour (steam) condition is indicated when the broad range infrared detector 16c detects radiation above the reference, and the narrow band infrared detector 16d (2.63 μm band) and the microwave detector 16f both detect radiation below the reference; (d) and a smoke or soot condition is indicated when the ultraviolet detector 16a, the visible light detector 16b, and the two narrow infrared bands detectors 16d and 16e all detect radiation below the detects radiation above the reference.

While the above table, and particularly the flow chart illustrated in FIG. 1a, include a large number of different conditions that may be detected in addition to the presence of the hydrocarbon vapour, it will be appreciated that simpler and less sophisticated systems could be used wherein not all of the above conditions are to be detected.

The two windows 13, 14 in test chamber 10 (FIG. 1) may be kept clean by known water and fuel repelling coatings. Another way of keeping the windows clean is to subject their inner surfaces to a flow of nitrogen or air, thereby also creating a positive pressure and preventing droplets and dirt from collecting on these surfaces.

Following is another example of a setup as illustrated in FIG. 1 and as described above with respect to FIG. 1a:

The radiation means 15 may be a quartz zenon flashlamp, which emits radiation from 0.2 to 4.4 microns. The detector unit 16 includes seven sensors, five being in the IR, and the remaining two being in the UV spectral ranges.

The two UV sensors include two silicone sensors, one with a 0.26 micron filter, and the other with a 0.3 micron filter. The 0.26 micron wavelength is strongly absorbed by aeromatic flammable vapours, while the 0.3 micron wavelength is not influenced by those vapours.

The five IR sensors are for the following spectral ranges:

(a) 2.7 micron, which wavelength is absorbed in water vapour;

(b) 3.4 micron, which wavelength is absorbed by any vapour gas containing the C—H chemical bond (practically any flammable gas);

(c) 4.0 micron, which wavelength is not absorbed by atmospheric air or flammable gas/vapours;

(d) 4.4 micron, which wavelength is strongly emitted by fire; and (e) 4.0 micron, which wavelength is weakly emitted by fire.

The first three IR sensors may be placed on three focal points of the IR optics; while the last two IR sensors may be placed so that they have a 90° field of view.

The algorithm for measuring flammable gas and water-vapour concentration in the space between the radiation source and the detector units is based on the changing ratio of measured radiation between the reference wavelength sensors and the absorbed wavelength sensors. As a concentration of flammable gas (water vapour) increases, the measured radiation of the absorbed wavelengths decreases, while the measured radiation of the reference wavelengths remains almost the same. The result is that the ratio between the readings of the two sensors is changed from the initial ratio. In this case, the absorbed wavelength is 3.4 microns for flammable gas, and 2.7 microns for water vapour, while the reference wavelength is 4.0 microns for both cases.

The formula that determines the concentration of flammable (water vapour) gas as a function of the changing ratio between the absorbed wavelengths radiation and the reference wavelength radiation is:

$$C = [ln(q_o) - ln(q)]/a$$

wherein:

C—flammable (water vapour) gas concentration;

$q_o$—the ratio in a clean environment between the peak flash radiation measured by the sensor with observed wavelength filter and the sensor with reference wavelength filter;

q—the same as $q_o$ in an environment containing flammable gas (water vapour); and a—an experimental parameter depending on the sensors, the gas, and the distance between the radiation source and the detector unit.

The algorithm for fire detection is based on the strong 4.4 emission line, typical for all organic fire spectra. In the presence of fire, the sensor with 4.4 micron filter will receive significantly more radiation than the sensor with 4.0 micron filter. In the presence of other common sources of radiation (lamps, sun), the situation will be reversed; therefore, an increase of the 4.4 micron radiation, greater than the increase of the 4.0 radiation, is an indication of a fire event.

Figure 2:
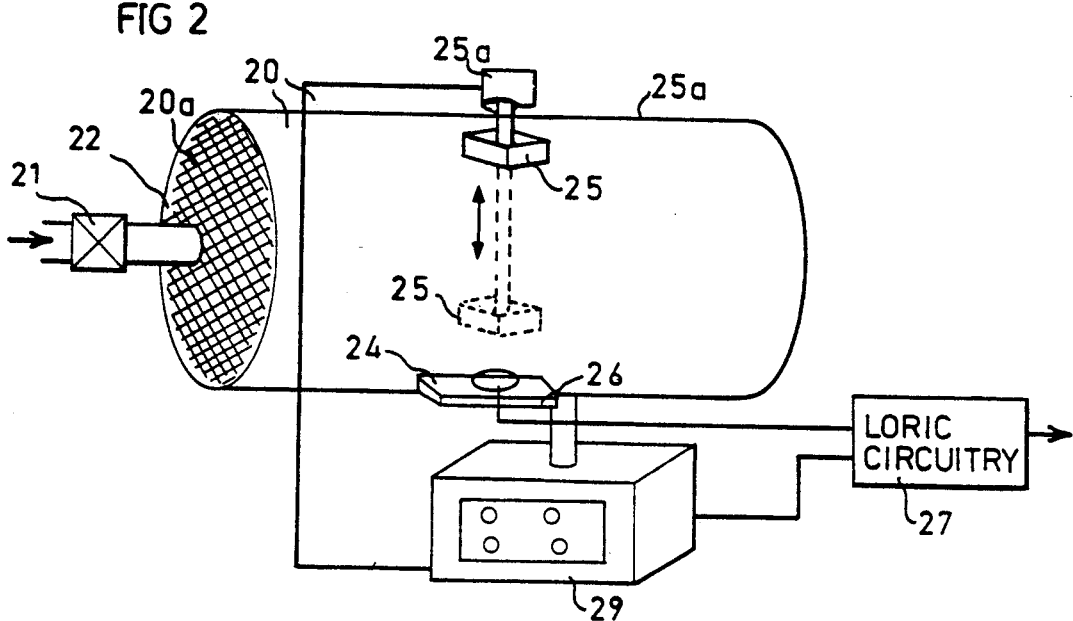
Figure 2A:
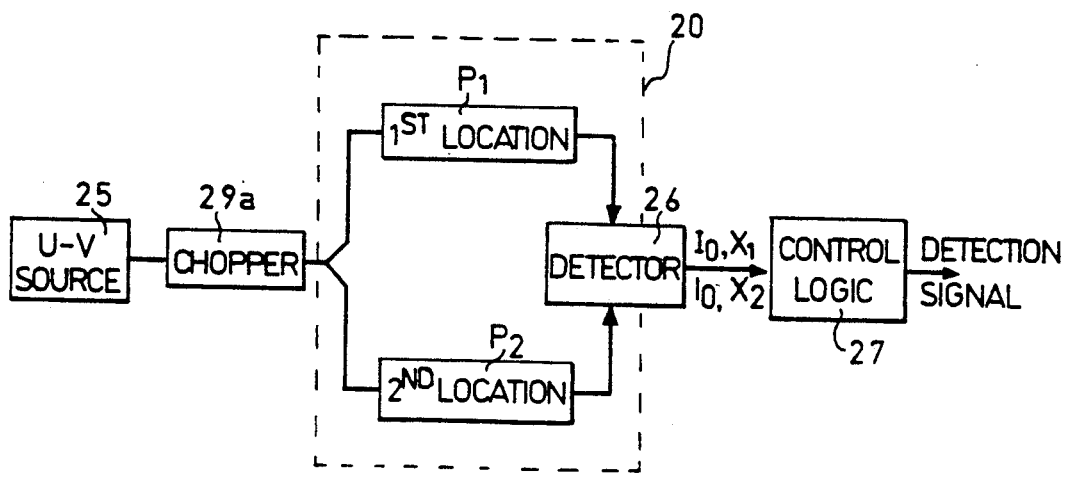
FIGS. 2a, 4a and 5a are block diagrams illustrating the essential components and the electrical circuitry in the systems of FIGS. 2, 4 and 5, respectively.

The System of FIGS. 2 and 2a

FIG. 2 illustrates another arrangement which also includes a test chamber 20 having an inlet 20a adapted to receive air from the monitored area as pumped by a pump 21, and/or as received through a semipermerable membrane 22 at the inlet end 20a. In this case, the radiation unit 25 is mounted internally within the test chamber 20 on a carriage 25a which moves the radiation unit towards and away from the window 24. The radiation, after its attenuation by the gas within the test chamber, is received by the radiation detector 26 mounted externally of the test chamber in alignment with window 24.

Carriage 25a is controlled by a processor 29 to reciprocate the radiation unit 25 from a distal position, as shown in full lines in FIG. 2, to a proximal position, as shown in broken lines in FIG. 2, with respect to detector 26. This movement of the radiation unit may be at a rate, for example, of two reciprocations per second. The radiation detector 26 is controlled by the processor 29 to feed its output to the logic circuitry 27 when the radiation unit 25 is both at its distal and proximal positions. The logic circuitry will thus output two signals according to the attenuation of the radiation at these two instantaneous positions of the radiation source.

FIG. 2a illustrates the operation of the system in the arrangement of FIG. 2. When the radiation unit 25 is in its distal position, shown in full lines in FIG. 2 and indicated at $P_1$ in FIG. 2a, there is a long optical path (indicated as $X_1$) between the radiation unit 25 and the detector 26. When the radiation unit is at its proximal position, shown in broken lines in FIG. 2 and indicated at $P_2$ in FIG. 2a, the optical path ($X_2$) to the detector is much shorter.

Thus, detector 26 will output a first electrical signal ($I_o$, $X_1$) when the radiation unit is in its distal position $P_1$, and a second signal ($I_o$, $X_2$) when the radiation unit is in its proximal position $P_2$. Since the two locations $P_1$ and $P_2$ are known and constant, the arrangement illustrated in FIG. 2 removes the influences of relatively constant conditions, such as dirt on the windows, condensation, etc., and thereby the logic circuitry 27 produces an output more accurately indicating the degree of attenuation of radiation by the gas within the test chamber.

As shown in FIG. 2a, the radiation unit 25 is also modulated at a predetermined frequency by processor 29, as schematically indicated by block 29a in FIG. 2a. This modulating frequency is also applied by the processor to the logic circuitry 27, as described above with respect to the FIG. 1 embodiment.

It will be appreciated that the system illustrated in FIG. 2, as well as the systems in FIGS. 3-5 to be described below, may apply radiation in one or more of the spectral ranges described above with respect to FIG. 1, particularly as illustrated in the flow chart of FIG. 1a and the corresponding table, in order to detect, and discriminate between, the many different conditions as illustrated in the table.

Figure 3:
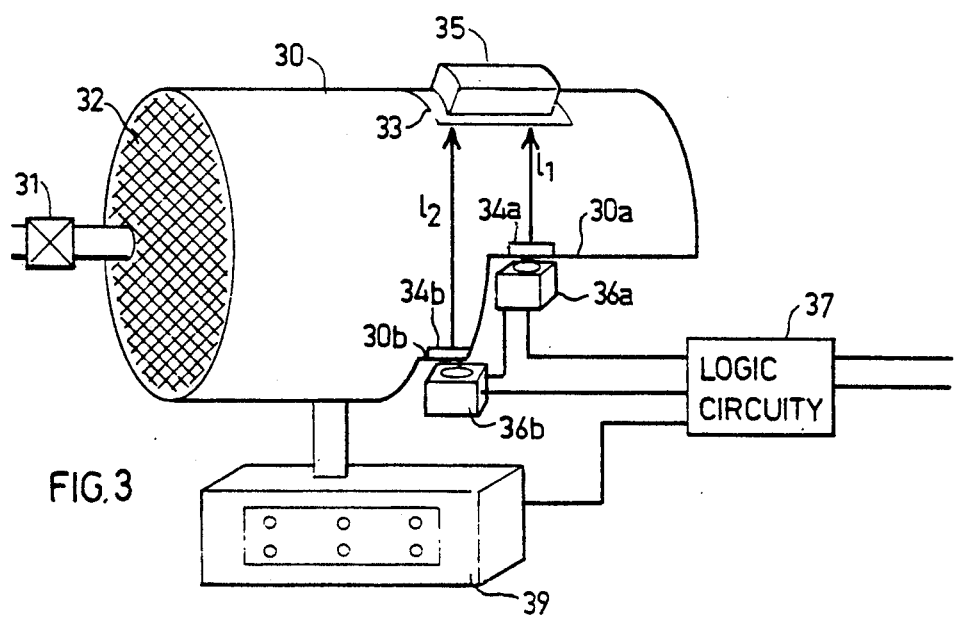

The System of FIG. 3

FIG. 3 illustrates a further implementation, also including a test chamber 30 into which air from the monitored area is fed by a pump 31 and/or via a semipermeable membrane 32. The test chamber 30 also includes a window 33 through which radiation from the radiation unit 35 passes into the test chamber 30. In this case, however, the test chamber is formed with a "knee" bend to provide a section 30a of relatively small diameter and another section 30b of larger diameter. Test chamber section 30a is provided with a window 34a cooperable with an external radiation detector 36a, and test chamber section 30b is provided with a window 34b cooperable with an external radiation detector 36b. Both detectors are irradiated by an external radiation unit 35 via a window 33.

It will thus be seen that the two detectors 36a, 36b, are located at distance $l_1$ and $l_2$, respectively, from the radiation unit 35. Thus, the attenuation signal o is calculated by the relation:

$$\alpha = \frac{\frac{Ia}{\ln} Ib}{l_1 l_2}$$

where:

Ia is the output from detector 36a;

Ib is the output from detector 36b;

$l_1$ is the distance of detector 36a from radiation source 35; and $l_2$ is the distance of detector 36b from radiation source 35.

The main advantage of the implementation illustrated in FIG. 3 is the independence of the output signals on the stability of the electronic circuit elements, the power supply, temperature variations, and the ageing of the detectors and other elements of the electronic circuit.

In all other respects, the arrangement illustrated in FIG. 3, including the operation of the processor 39, is the same as described above with respect to FIGS. 1 and 2.

Figure 4:
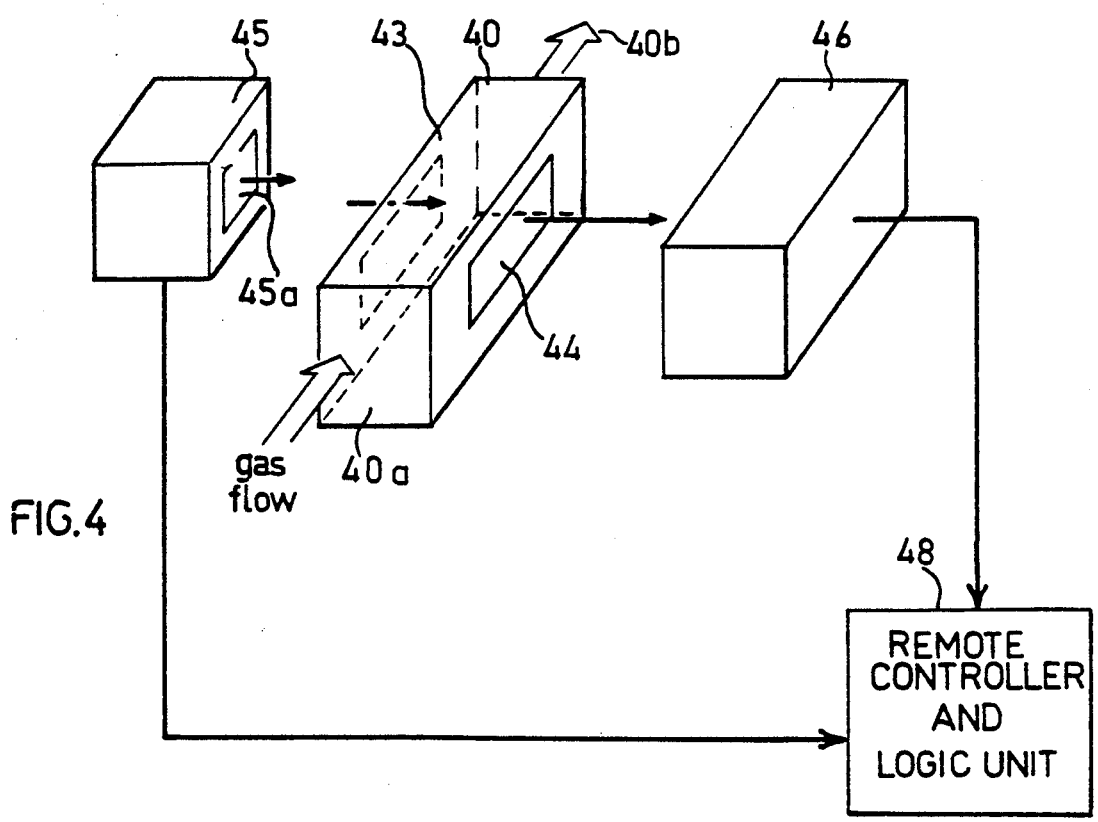

The System of FIG. 4

FIG. 4 illustrates an arrangement wherein the system is constructed of a plurality of modular units which can be assembled as desired. Thus, the system illustrated in FIG. 4 includes a test chamber 40 in the form of one modular unit and having an inlet 40a at one end, an outlet 40b at the opposite end, and windows 43 and 44 on its opposite sides transversely of the flowpath of the air from the inlet to the outlet. The system of FIG. 4 further includes: a radiation unit 45 in the form of a separate modular unit having an output window 45a alignable with window 43 of the test chamber modular unit 40; a detector modular unit 46 having a similar window (not shown) alignable with window 44 of the test chamber unit 40; and a remote controller and logic unit 48 incorporating all the elements of the processor and logic circuitry described above, e.g., 19 and 17 in FIG. 1.

The test chamber modular unit 40 may also include a pump 41 (FIG. 4a) for pumping air from the monitored area into its inlet 40a, e.g., via a semipermeable membrane, and may also include an exit or release valve at its outlet end 40b for outletting the air flowing through the test chamber. All the above modular units 40, 45, 46 and 48, may have suitable "plug-in" connections for connecting them together electrically, optically and mechanically.

Figure 4A:
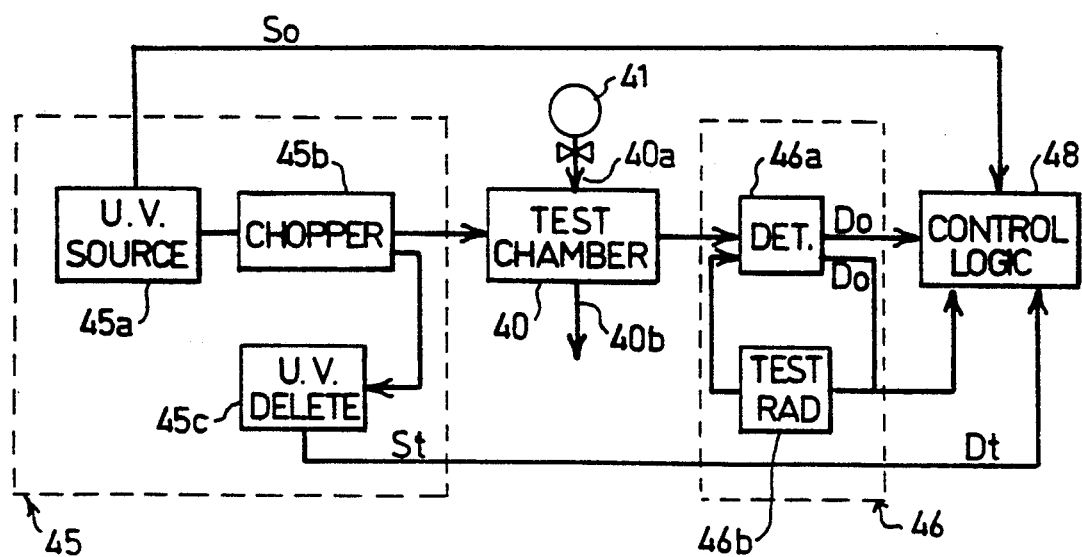

The contents of each of the modular units 40, particularly the radiation unit 45 and the detection unit 46, are more particularly illustrated in FIG. 4a.

Thus, the radiation unit 45 includes a radiation source 45a and a chopper 45b for modulating the radiation which is transmitted to the test chamber in modular unit 40. Modular unit 45 further includes a test detector 45c which is also exposed to the radiation outputted from the chopper 45b. Detector 45c produces a test signal (St) which is fed directly to the control logic unit 48, together with the original signal (So) from the radiation source 45a.

The detector modular unit 46 includes a detector 46a which detects the radiation from the test chamber 40 and outputs the signal (Do) to the control logic 48. Detector unit 46 further includes a test radiation source 46b which also exposes the detector 46a to test radiation, the latter outputting a test signal (Dt) to the control logic 48.

When So/St is greater than "1", a first "detection" signal is received by the control logic 48; and when Do/Dt is greater than "1", a second "detection" signal is received at the control logic. Thus, the occurrence of one such "detection" signal will indicate the first occurrence of vapours in the vicinity, and the occurrence of both "detection" signals will indicate that the vapour has filled the monitored space. The actual meaurement will take place when both "detection" signals have occurred within a predetermined time interval (e.g., 1-10 seconds). The ratio of So/St and Do/Dt will also indicate undue attentuation by spurious means, e.g., dirty windows in the modular units, and will provide a signal to this effect.

Figure 5:
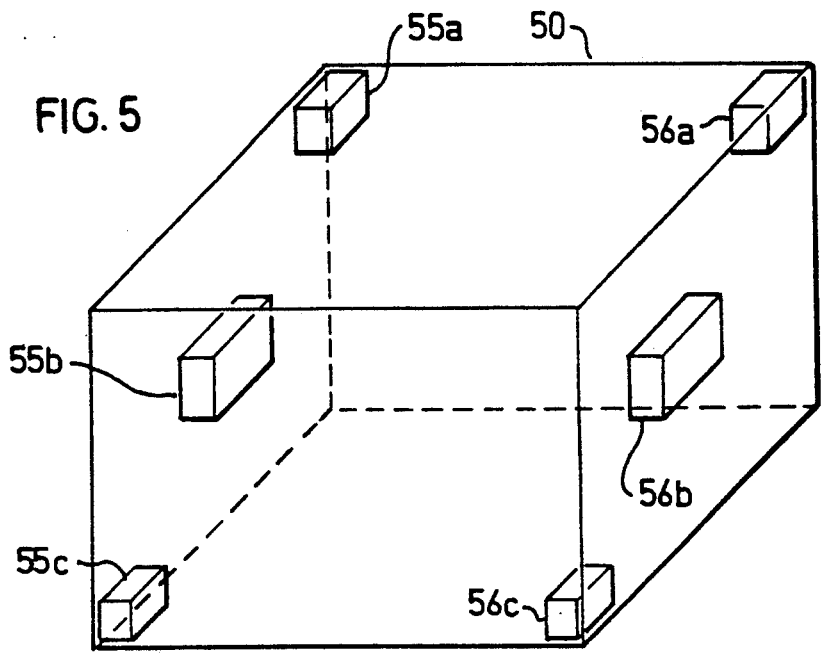
Figure 5A:
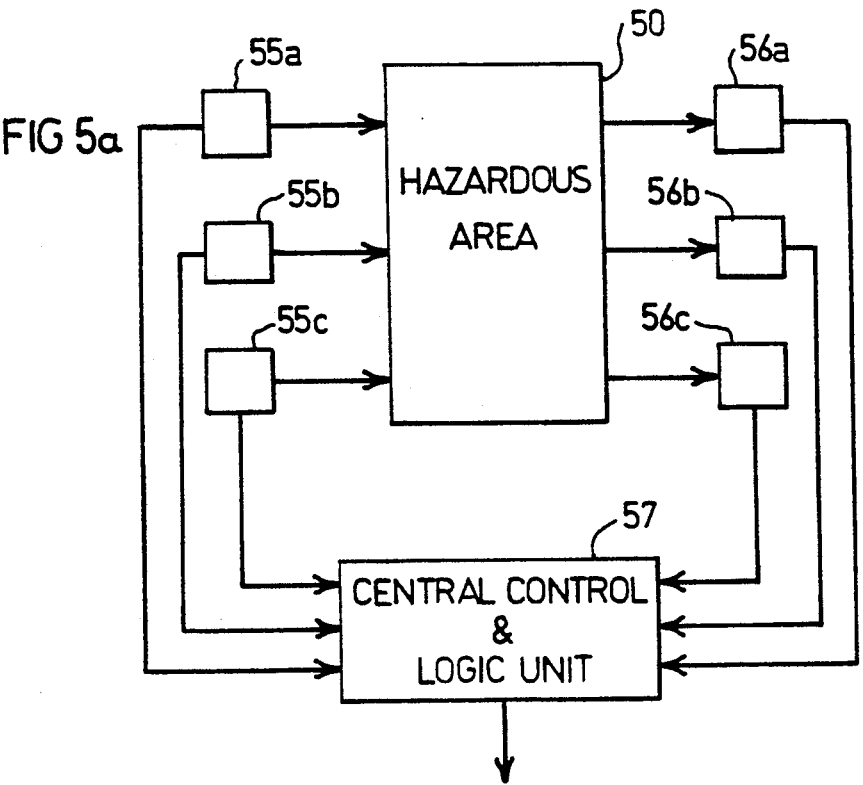

The System of FIGS. 5 and 5a

In all the above described arrangements, a gas sample is fed from the monitored area to the test chamber where the tests are made. FIGS. 5 and 5a illustrate an arrangement wherein the gas in the monitored area is directly and continuously tested.

Thus, as shown in FIGS. 5 and 5a, the monitored area, generally designated 50, includes a plurality of radiation units 55a-55c at different locations on one side of the monitored area 50, and a plurality of detector units 56a-56c on the opposite side of the monitored area 50, each aligned with one of the radiation units 55a-55c. All the radiation units and detector units are controlled by a remote central control and logic unit 57. Cross-correlation between the various detector units 56a-56c allows full coverage of the monitored area.

As indicated earlier, the systems of FIGS. 2-5 can test for all of the spectral ranges, or any number of them, described above with respect to the system of FIG. 1, particularly the flow chart of FIG. 1a and the table relative to it. Thus, all of the above systems may test not only for the presence of a predetermined hydrocarbon vapour deviating from a predetermined concentration, such as one indicating a possible flammable or explosive atmosphere, or merely one deviating from a "clean" atmosphere a predetermined amount, but also for the presence of flame, water vapour, smoke and/or soot particles which may indicate that a fire has already started.

While the invention has been described with respect to several preferred embodiments, it will be appreciated that these are set forth merely for purposes of example, and that many other variations, modifications and applications of the invention may be made.

What is claimed is:

1. A method of detecting the presence of a predetermined hydrocarbon vapour of a predetermined concentration in a monitored area, comprising:
   exposing gas in or from the monitored area to radiation emitted from a flashlamp which emits both ultraviolet radiation and infrared radiation;
   detecting ultraviolet radiation within a predetermined ultraviolet spectral range, and infrared radiation within a predetermined infrared spectral range, after the radiation emitted from said flashlamp has passed through said gas;
   and comparing said detected ultraviolet radiation and infrared radiation with a reference of predetermined attenuation characteristics of said hydrocarbon vapour and concentration in said ultraviolet nd infrared spectral ranges.

2. The method according to claim 1, wherein said ultraviolet spectral range is from 0.1–0.4 μm, detected radiation below said reference providing an indication of the presence of said hydrocarbon vapour in said monitored area at a concentration producing a possible flammable or explosive atmosphere.

3. The method according to claim 1, wherein said infrared spectral range is 1–3.5 μm, the detected radiation above said reference providing an indication of the presence of water vapour, flame, and/or smoke in said monitored area.

4. The method according to claim 3, wherein said predetermined infrared spectral range includes at least two narrow bands, and said detected radiation is compared with a reference of predetermined attenuation characteristics in each of said narrow bands.

5. The method according to claim 4, wherein said predetermined infrared spectral range includes the 2.63 μm band and the 4.3 μm band, the detected radiation below said reference in the 2.63 μm band providing an indication of the presence of water vapour, flame and/or smoke in the monitored area, and the detected radiation above said reference in the 4.3 μm band providing an indication of the presence of flame and/or smoke in the monitored area.

6. The method according to claim 1, wherein said radiation emitted from said flashlamp and to which the gas is exposed also includes visible light from the 0.4–0.8 μm spectral range, and said detected radiation is also compared with a reference of predetermined attenuation characteristics in said visible light band, detected radiation above said latter reference indicating the presence of water vapour or a flame in the monitored area, and detected radiation below said latter reference indicating smoke and/or soot particles in the monitored area.

7. The method according to claim 1, wherein said radiation emitted from said flashlamp and to which the gas is exposed also includes radiation in the microwave spectral range, and said detected radiation is also compared with a reference of predetermined attenuation characteristics in said microwave spectral range; the detected radiation below said latter reference indicating the presence of water vapour and/or a flame in the monitored area.

8. The method of claim 1, wherein said flashlamp is a quarts Xenon flashlamp.

9. Apparatus for detecting the presence of a predetermined hydrocarbon vapour of a predetermined concentration in a monitored area, comprising:
   a flashlamp radiation means which emits both ultraviolet radiation and infrared radiation;
   means for exposing gas in or from the monitored area to the radiation emitted by said flashlamp radiation means;
   detector means for detecting ultraviolet radiation within a predetermined ultraviolet spectral range, and infrared radiation within a predetermined infrared spectral range, after the radiation emitted from said flashlamp has passed through said gas;
   and comparing means for comparing said detected ultraviolet and radiation infrared radiation with a reference of predetermined attenuation characteristics of said hydrocarbon vapour and concentration in said ultraviolet and infrared spectral ranges.

10. The apparatus according to claim 9, wherein said ultraviolet spectral range is from 0.1–0.4 μm, detected radiation below said reference providing an indication of the presence of said hydrocarbon vapour in said monitored area at a concentration producing a possible flammable or explosive atmosphere.

11. The apparatus according to claim 9, wherein said flashlamp radiation means includes a quartz Xenon flashlamp.

12. The apparatus according to claim 9, wherein said infrared spectral range is 1–3.5 μm, the detected radiation above said reference providing an indication of the presence of water vapour, flame, and/or smoke in said monitored area.

13. The apparatus according to claim 12, wherein said predetermined infrared spectral range includes at least two narrow bands, and said detected radiation is compared with a reference of predetermined attenuation characteristics in each of said narrow bands.

14. The apparatus according to claim 13, wherein said predetermined infrared spectral range includes the 2.63 μm band and the 4.3 μm band, the detected radiation below said reference in the 2.63 μm band providing an indication of the presence of water vapour, flame and/or smoke in the monitored area, and the detected radiation above said reference in the 4.3 μm band providing an indication of the presence of flame and/or smoke in the monitored area.

15. The apparatus according to claim 9, wherein said flashlamp radiation means also emits visible light from the 0.4–0.8 μm spectral range, and said comparing means compares said detected radiation also with a reference of predetermined attenuation characteristics in said visible light band, detected radiation above said latter reference indicating the presence of water vapour or a flame in the monitored area, and detected radiation below said latter reference indicating smoke and/or soot particles in the monitored area.

16. The apparatus according to claim 9, wherein said flashlamp radiation means also emits radiation in the microwave spectral range, and said comparing means compares said detected radiation also with a reference of predetermined attenuation characteristics in said microwave spectral range; the detected radiation below said latter reference indicating the presence of water vapour and/or a flame in the monitored area.

17. The apparatus according to claim 9 particularly useful for detecting the presence of a predetermined hydrocarbon vapor of a predetermined concentration in a monitored area indicating a flammable or explosive atmosphere, or an atmosphere in which a fire has already started, wherein said comparing means comprises:
logic circuitry for receiving an output indicating the magnitude of the ultraviolet radiation within said predetermined ultraviolet spectral range received thereby, for comparing same with a reference of predetermined attenuation characteristics of said predetermined hydrocarbon vapour and concentration in said spectral range, and for providing an electrical output indicative of the presence of said predetermined hydrocarbon vapour and concentration in the gas exposed to said radiation.

18. The apparatus according to claim 17, further including a test chamber having an inlet connected to said monitored area for receiving gas therefrom, and a flowpath through which the gas flows to an outlet; said flashlamp radiation means and detector means being on opposite sides of said flowpath.

19. The apparatus according to claim 18, wherein at least one of said flashlamp radiation means and said detector means is external to the test chamber, and said test chamber includes a window through which the external at least one of said flashlamp radiation means and said detector means is aligned.

20. The apparatus according to claim 18, wherein at least one of said flashlamp radiation means and said detector means is movable within said test chamber from a first position with respect to the other of said at least one of said flashlamp radiation means and said detector means, to a second position closer to the other of said at least one of said flashlamp radiation means and said detector means; said logic circuitry receiving the outputs of said detector means in both positions of said movable means, and subtracting one output from the other for determining and removing the influences of relatively constant conditions, such as dirt, condensation, and the like.

21. The apparatus according to claim 20, wherein said movable means is the flashlamp radiation means.

22. The apparatus according to claim 18, wherein said test chamber includes two sections of different transverse dimensions in the flowpath of the gas, said detector means including two sections, one on each of said two different transverse dimensions, and both aligned with said flashlamp radiation means; said logic circuitry receiving the outputs from both sections of said detector means and subtracting one output from the other for determining and removing the influences of relatively constant conditions, such as dirt, condensation, and the like.

23. The apparatus according to claim 18, wherein the inlet of said test chamber is connected by a pump to said monitored area.

24. The apparatus according to claim 18 wherein the inlet of said test chamber is connected by a semi-permeable membrane to said monitored area.

25. The apparatus according to claim 18, wherein said system is constructed of a plurality of modular units, including: a first modular unit containing said test chamber; a second modular unit containing said flashlamp radiation means and to be located on one side of said test chamber; a third modular unit containing said detector means and to be located on the opposite side of said test chamber; and a fourth modular unit containing said logic circuitry.

26. The apparatus according to claim 25, wherein:
said second modulator unit includes a test detector also exposed to said flashlamp radiation means therein;
said third modular unit includes a test radiation source also exposing said detector means therein;
and said logic circuitry in the fourth modular unit includes inputs from said flashlamp radiation means and test detector in the second modular unit, and from said detector means and test radiation source from said third modular unit, and is effective to indicate undue attenuation of the radiation during the passage of the radiation from said second modular unit through said first modular unit and to said third modular unit.

27. The apparatus according to claim 17, wherein said flashlamp radiation means and said detector means act directly on the gas in the monitored area.

28. The apparatus according to claim 27, wherein said flashlamp radiation means includes a plurality of radiation unit at different locations on one side of said monitored area, and said detector means includes a plurality of detector units on the opposite side of said monitored area and each 29. The apparatus according to claim 17, wherein said flashlamp radiation means is modulated according to a predetermined frequency, and the output of said detector means received in said logic circuitry is also modulated according to said predetermined frequency.

30. The apparatus according to claim 17, wherein said flashlamp radiation means also radiates infrared radiation in a predetermined infrared spectral range; and said logic circuitry also compares the detected radiation with a reference of predetermined attenuation characteristics in said predetermined infrared spectral range.

31. The apparatus according to claim 17, wherein said flashlamp radiation means also radiates visible light in a predetermined visible light spectral range, and said logic circuitry also compares the detected radiation with a reference to predetermined attentuation characteristics in said predetermined visible light spectral range.

32. The apparatus according to claim 17, wherein said radiation means also radiates microwave radiation in a predetermined microwave spectral range, and said logic circuitry also compares the detected radiation with a reference of predetermined attenuation characteristics in said predetermined microwave spectral range.

* * * * *

UNITED STATES PATENT AND TRADEMARK OFFICE
CERTIFICATE OF CORRECTION

PATENT NO. : 5,281,816
DATED : January 25, 1994
INVENTOR(S) : Esther Jacobson, et. al.

It is certified that error appears in the above-indentified patent and that said Letters Patent is hereby corrected as shown below:

-Claim 1, Column 11, line 29, replace "nd" with --and--

-Claim 8, Column 12, line 9, replace "quarts" with --quartz--

-Claim 28, Column 14, line 36, replace "unit" with --units--

-Claim 28, Column 14, line 39, replace "and each"
with --and each aligned with one of said radiation units.--

Signed and Sealed this

Thirtieth Day of January, 1996

Attest:

BRUCE LEHMAN

*Attesting Officer*    *Commissioner of Patents and Trademarks*